(12) United States Patent
Islam

(10) Patent No.: US 6,603,560 B1
(45) Date of Patent: Aug. 5, 2003

(54) HIGH SENSITIVITY FIBER OPTIC INTERFEROMETRIC MEMS

(75) Inventor: Mohammed N. Islam, Allen, TX (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 09/805,623

(22) Filed: Mar. 13, 2001

Related U.S. Application Data

(60) Provisional application No. 60/189,525, filed on Mar. 15, 2000.

(51) Int. Cl.[7] .................................................. G02F 1/21
(52) U.S. Cl. ........................................ 356/480; 356/5.09
(58) Field of Search ............................... 356/490, 5.09, 356/32, 477, 478, 345, 349, 346, 352; 350/354; 385/1

(56) References Cited

U.S. PATENT DOCUMENTS

| | | | |
|---|---|---|---|
| 4,854,676 A | * | 8/1989 | Kalyanaraman et al. .... 350/354 |
| 5,898,517 A | * | 4/1999 | Weis .......................... 356/5.09 |
| 5,917,966 A | * | 6/1999 | Beuhler et al. ................ 385/12 |
| 5,986,759 A | * | 11/1999 | DeCain et al. .............. 356/345 |
| 6,160,627 A | * | 12/2000 | Ahn et al. ................... 356/477 |

* cited by examiner

Primary Examiner—Constantine Hannaher
Assistant Examiner—Otilia Gabor
(74) Attorney, Agent, or Firm—Baker Botts L.L.P.

(57) ABSTRACT

One aspect of the invention relates to an optical signal processing device including a Mach-Zehnder interferometer which includes a reference arm comprising a first Fabry Perot interferometer and a sample arm comprising a second Fabry Perot interferometer including at least two mirrors forming a Fabry-Perot cavity therebetween, and an adsorbing material disposed within the cavity. The Fabry-Perot interferometer in the sample arm permits a first portion of an input signal to pass multiple times through the sample while a second portion of the input signal passes through the reference arm, and the first and second signal portions are combined at an output to result in constructive or destructive interference between the signal portions.

5 Claims, 4 Drawing Sheets

☐ Si    ▨ SiN    ▨ Poly-Si    ▨ PSG    ▨ Metal

☐ Si    ▨ SiN    ▨ Poly-Si    ▨ PSG    ▨ Metal

HIGH SENSITIVITY FIBER OPTIC INTERFEROMETRIC MEMS

RELATED APPLICATION

This application claims the benefit of U.S. Provisional Application Ser. No. 60/189,525, filed Mar. 15, 2000.

TECHNICAL FIELD OF THE INVENTION

The present invention relates to generally the field of communication systems and more particularly to a high sensitivity fiber optic interferometric MEMS device.

BACKGROUND OF THE INVENTION

A significant obstacle to widespread application of optical transducers to chemical and biochemical sensors on a large scale is equipment cost and ease of use. Traditional spectroscopic and interferometric techniques widely used for both qualitative and quantitative determinations are bulky, expensive, laboratory systems requiring trained technicians for data acquisition and interpretation. On the other hand, cross-disciplinary applications of optical transducers require simple, low-cost, low-maintenance approaches technically accessible to non-specialists, with cheap disposable probes and compact associated electronics. Despite the low-cost features, it is desirable to provide sensitivities comparable to laboratory instruments to ensure accurate and reliable diagnoses.

Although strides have been made to apply integration and miniaturization to cost reduction, key components of many optical sensor systems still employ traditional methods to achieve high resolution and sensitivity. For example, current fiber-optic spectroscopic sensors use high-dispersion spectrometers [1] to obtain high resolution. Micro-machined spectrometers have been demonstrated and offer the possibility of integrating both dispersion and detection; however, resolution is low [2]. Miniature interferometers [3] have also been demonstrated and applied to $CO_2$ determination [4].

SUMMARY OF THE INVENTION

One aspect of the present invention comprises a high-sensitivity chemical or biochemical sensor based on a Fiber-optic Interferometric MEMS (FIMS) device. In a particular embodiment, the FIMS comprises two micro-electromechanical system (MEMS)-based Fabry-Perot interferometers (FPI) placed at the tip of a fiber-optic cable. The behavior of the FIMS is approximately equivalent to two FPI's placed in a Mach-Zehnder interferometer. The two MEMS FPI's are operated in parallel, with one acting as a reference and the other containing the adsorbing material sensitive to the target bio/chemical agent. The Mach-Zehnder interferometer is implemented by overlapping the transmitted or reflected signal from the MEMS devices with the mode of a single mode fiber.

Another aspect of the invention relates to an optical signal processing device comprising a Mach-Zehnder interferometer which includes a reference arm comprising a first Fabry Perot interferometer and a sample arm comprising a second Fabry Perot interferometer. The second Fabry Perot interferometer includes at least two mirrors forming a Fabry-Perot cavity therebetween, and an adsorbing material disposed within the cavity. The Fabry-Perot interferometer in the sample arm permits a first portion of an input signal to pass multiple times through the sample while a second portion of the input signal passes through the reference arm, and the first and second signal portions are combined at an output to result in constructive or destructive interference between the signal portions.

The FIMS device can act, for example, as a flexible, high-sensitivity bio-chemical sensor for a number of reasons. First, the FPI's provide effective "gain" by multi-passing the sample under test. Second, the Mach-Zehnder interferometer allows for an "off-null" measurement by differencing the arm under test with the reference arm. Since the two FPI's can be constructed on the same substrate and mounted side-by-side, the Mach-Zehnder is insensitive to many common mode fluctuations. Finally, the FIMS can be operated in a number of modes with high-sensitivity and great flexibility by tuning or biasing the two FPI's independently.

Various aspects of the present invention may exhibit some or all of the following characteristics:
  compatible with fiber-optics;
  high-sensitivity with off-null measurements;
  flexible and insensitive to background fluctuations;
  low-cost and easily manufacturable; and
  compact, robust and reliable.

Particular embodiments of the FIMS device satisfy the above criteria with a very simple design. The design can be inherently compatible with fiber-optics by interfacing the output and input through a single-mode fiber. High-sensitivity with off-null measurement capability can be achieved by differential mode detection against an adjustable reference arm. The design is flexible because the two FPI's can be biased or tuned independently, and background fluctuations can be desensitized by growing the two FPI's on the same substrate next to one-another. The FIMS device can use standard CMOS processing steps, so it is low-cost and easily manufacturable. Finally, it can be made compact, robust and reliable by, for example, packaging at the tip of a fiber. Moreover, the design can be made an entirely planar structure, and the maximum motion required by any of the MEMS elements is a quarter wavelength.

The approach proposed here substantially reduces sensor cost. It takes advantage of the mass production techniques well-known in the semiconductor industry and applied to micro-machines to substantially reduce instrument footprint by integrating a key component of the optical system, the spectral discriminator, into the sensing head. In traditional systems, this component is usually the largest and most expensive. By combining interferometric and differential detection techniques, the FIMS device is expected to provide high sensitivity and background rejection. The concept can be applied to selective interactions for both qualitative and quantitative determinations.

The device geometry is simple and can be used for several measurements—spectrophotometry, luminescence spectroscopy, and refractometry. In other words, it constitutes several instruments in one. In addition, the combination of interferometric techniques that include an internal phase reference that is expected to lead to high background noise rejection minimizes calibration drift when used for absorption measurements, for example. Thus, the combination of phase sensitive detection and micro-machining yields miniature, easy to use, yet reliable, sensors with performance comparable to more expensive and bulky units at significantly reduced cost.

Fabrication of the MEMS-based FIMS device and integration with fiber optics will provide sensors to serve as the tentacles for the fiber-optic information superhighway. The optic designing and optical testing of the FIMS device will identify optimal biasing and operating conditions for the FIMS for high-sensitivity and/or off-null measurements. The collaboration with chemists and bio-chemists will lead to integration of the adsorbing material into the FIMS device and testing of the sensor in realistic applications along with sample preparation and aggregation. In addition, the scaling up of the FIMS device into array sensors and investigation of other applications of the FIMS building block will broaden the range of applications for the FIMS.

BRIEF DESCRIPTION OF THE DRAWINGS

For a more complete understanding of the present invention, and for further features and advantages thereof, reference is now made to the following description taken in conjunction with the accompanying drawings, in which.

DETAILED DESCRIPTION OF THE INVENTION

Figure 1:
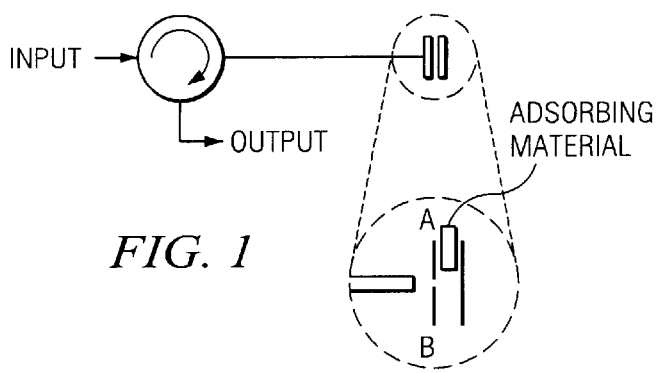
FIG. 1 is a schematic of one particular example embodiment of a FIMS device used in reflection mode according to the teachings of the present invention.
Figure 2:
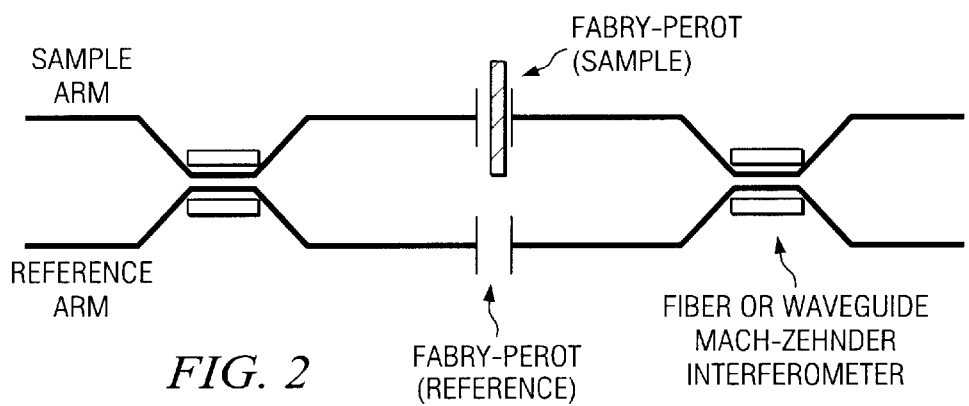
FIG. 2 is one example of a configuration of an interferometric micro-sensor, comprising a fiber or waveguide Mach-Zehnder interferometer and two independent Fabry-Perot interferometers constructed according to the teachings of the present invention.

Fiber optic systems are becoming the brick and mortar on which information systems ride. The chemical, biochemical or pressure sensors used in civilian and military applications are going to be the tentacles that feed into the information systems. Therefore, one aspect of this invention recognizes that it is important to develop a category of lightweight and environmentally stable sensors that directly interface to fiber-optic systems.

The fiber-optic based sensors should be of high-sensitivity, flexible in design, compact, lightweight, rugged and low-cost. MEMS technology provides a mature platform in which such sensors can be constructed because MEMS uses standard integrated circuit processing techniques to implement novel, miniature structures. The ideal sensors would be MEMS devices that connect and take advantage of the fiber-optic technologies used in telecommunication systems.

The present invention recognizes that for commercial and military applications in chemical, biochemical and pressure sensing, there is a need for a compact, low-cost, rugged, high-sensitivity probe that mates with fiber-optic systems. These challenges can best be met by merging the mature technologies of fiber optics with MEMS devices. More specifically, the FIMS device combines the MEMS-based Fabry Perot Interferometers (FPI's) with a Mach-Zehnder interferometer formed by overlapping the transmitted or reflected beam through the FPI's with the spatial mode of a single mode fiber.

The FIMS device combines the MEMS planar technology with fiber-optics, using unique features of the interface of MEMS to the modes of single-mode fibers. Two FPI's are created on a silicon substrate using standard CMOS processing techniques. Then, the interference between the two arms (one reference and one with sample under test) and the overlap integral with the fiber-optic mode is used to create an "off-null" measurement.

Various aspects of the invention seek to develop a FIMS device that meets at least some of the criteria for most sensors to serve as a basic building block. These criteria for sensors include:
  compatible with fiber-optics
  high-sensitivity with off-null measurements
  flexible and insensitive to background fluctuations
  low-cost and easily manufacturable
  compact, robust and reliable
Various embodiments of certain aspects of the invention may achieve some or all of the following specifications:
  contrast ratio >10 dB;
  bandwidth in excess of 30 nm;
  high-sensitivity to detect changes of one part in $10^5$;
  reconfiguration speed of ~100 to 300ns;
  rugged, compact, environmentally stable packaging; and/or
  scalability to arrays of sensors of dimensions greater than ten.

Objectives and steps in developing the FIMS device include:
1. Develop the procedure for fabricating the MEMS-based FIMS device, which is a two-segment FPI. The size of the segments will be optimized for the performance in terms of speed and drive voltage while insuring compatibility with the fiber optics.
2. Interface the MEMS device with the fiber-optic system, where the spatial mode of the single mode fiber is used to form a simple Mach-Zehnder interferometer.
3. Compare and contrast the transmission and reflection operation of the FIMS devices. Identify the optimal operating conditions or biases for high-sensitivity and/or off-null measurements.
4. Optimize the trade-off between contrast ratio and bandwidth. Compare single layer FIMS structures with multiple-layer structures, and compare symmetric structures with asymmetric structures.
5. Identify the appropriate adsorbing material for detecting or sensing a target chemical or bio-chemical agent. Integrate the adsorbing material with the FIMS device for completing the biochemical sensor.

6. In collaboration with chemists or bio-chemists, test the FIMS sensor in a realistic application setting, including the steps of sample preparation and aggregation to increase the density of the agent.
7. Package the FIMS device into a compact, rugged, environmentally stable device.
8. Study means of fabricating an array of FIMS devices with dimensions greater than ten.
9. Investigate other applications of the FIMS building block in fields such as optical switching, pressure sensing, and environmental sensing.

The compact, FIMS device is shown schematically in FIG. 1, where the device is assumed to operate in the reflection mode (usually the higher contrast mode) . The specific FIMS device proposed herein has a number of advantageous features including:

"gain" by multi-passing the sample under test in a FPI;

difference mode operation by contrasting the test FPI with a reference FPI;

natural coupling properties of the single-mode fiber are used to create a Mach-Zehnder interferometer that permits optimal biasing or off-null measurements;

high-flexibility by adjusting the bias points of the two FPI's lock-in techniques can be used to further enhance sensitivity;

rapid sensing potential (i.e., ~100 ns or longer) because the device needs only to change the phase by PI or less, or a corresponding movement of a quarter of a wavelength; and high reliability because a completely planar structure with small motion of parts.

Moreover, the FIMS device is a key building block that can be used in a number of applications beyond chemical, biochemical or pressure sensing, such as switching, variable attenuation, spectral equalizers and displays. Thus, the invention is not intended to be limited to chemical, biochemical, or pressure sensing. Nevertheless, by way of example only, the following example describes use of the invention in the context of chemical and biochemical sensing.

Several fiber-optic devices applied in chemical and biochemical sensing rely on spectral changes associated with the analyte. For example, determinations using absorption measurements spectrally resolve changes in light intensity transmitted through the sample, determinations employing Raman scattering identify characteristic frequencies in the spectrum of light scattered by the analyte, and sample emission spectra are measured in methods employing luminescence. Thus, many fiber-optic sensors employ means to achieve spectral discrimination, usually relying on diffraction and interference effects. In other fiber-optic sensor applications, changes in optical path-length, such as occur through refractive index changes arising from adsorbates, are used to generate the signal of interest, interference effects again being commonly employed.

A primary design consideration in integrating spectrometers or refractometers into fiber-optic sensors is optimizing instrument performance while reducing unit cost. Traditional spectrometers are bulky, expensive systems mostly suited for laboratory measurements. However, there are numerous biochemical and chemical sensing applications that will benefit from compact, low cost instruments having sensitivity comparable to that of laboratory instruments.

A number of approaches based on integrated optics and MEMS for reducing unit size and cost have been proposed. Fabry-Perot, Mach-Zehnder and Michelson interferometers for sensor applications have been realized using integrated optics [5], and MEMS Fabry-Perot interferometers have been reported [6,7]. Fabry-Perot interferometers have high sensitivity, are tunable, and can provide "gain." Mach-Zehnder interferometers allow measurement in a differential mode wherein one arm of the interferometer is used as sample arm and the other arm provides a reference phase against which phase changes in the sample arm are compared at the output.

One aspect of the present invention comprises a novel sensor architecture combining increased sensitivity offered by the Fabry-Perot interferometer with background rejection achieved with differential measurement mode offered by the Mach-Zehnder configuration. The concept is shown schematically in FIG. 2. Fabry-Perot interferometers are placed in each arm of a Mach-Zehnder interferometer, one arm of which serves as reference. The sample is placed within the Fabry-Perot interferometer located in the other arm of the Mach-Zehnder structure.

The Fabry-Perot interferometer in the sample arm permits the optical signal to pass multiple times through the sample, thereby increasing sensitivity to small changes in optical path. The second Fabry-Perot interferometer provides a reference phase against which the phase changes in the sample arm is compared. The comparison is realized by the Mach-Zehnder configuration, in which the incoming probe light is split into two waves and recombined after traversal of the Fabry-Perot interferometers. The waves propagating in the two waves can thus experience different phase shifts and emerge in or out of phase. Subsequent interference between the waves can, therefore, be constructive or destructive. Since the independent Fabry-Perot interferometers enable tuning the relative phase difference, the sensor can be biased for high background rejection and sensitivity.

The basic sensor configuration may be realized in a simple way using optical fiber and MEMS. FIG. 3 shows such a realization employing a fiber-coupled MEMS device comprising two adjacent miniature Fabry-Perot interferometers. One of the Fabry-Perot interferometers is arranged to be sensitive to the analyte and the other is biased to provide a reference phase. Two configurations are possible, one in which the Fabry-Perot interferometers are operated in reflection mode and a single fiber is used to deliver both probe and information carrying beams. In the second configuration, the Fabry-Perot interferometers are operated in transmission mode and placed between two collinear fibers.

In each of the two configurations, the MEMS structure is placed symmetrically with respect to input and output fiber axes in such a manner that the incident wavefront is divided equally between the two Fabry-Perot interferometers. This arrangement essentially implements the beam splitter at the input to the Mach-Zehnder interferometer necessary to separate reference and sample beams. The beam combining function at the output of the Mach-Zehnder interferometer is implemented by coupling into a single fiber mode. Using a single-mode fiber in the input and output paths ensures the returning fields couple to the same waveguide mode and a high contrast between in-phase and out-of-phase modes of operation results.

The independent Fabry-Perot interferometers permit biasing the Mach-Zehnder interferometer to achieve high sensitivity and background rejection. The upper plot of FIG. 4 shows the transmission of a Fabry-Perot interferometer with 30% reflectivity mirrors enclosing a cavity of width d that contains a medium of refractive index n. $\lambda$ is the vacuum wavelength of the incident field, launched at an angle $\theta$ to the common normal of the mirrors and absorption is neglected. The lower plot shows the phase of the transmitted field. Since the two Fabry-Perot interferometers are independent, the phase difference between waves transmitted through them can be adjusted to yield destructive interference upon recombining the fields. For example, biasing the interferometers to operate at equivalent points of adjacent transmission peaks results in a relative phase shift of $\pi$, leading to destructive interference when the fields are recombined.

The increased sensitivity derives from the sharp slope of the Fabry-Perot interferometer response, which ensures large changes in signal with small changes in the optical path when high reflectivity, low absorption mirrors are used. For example, when the mirrors have identical reflectivities of 0.3 and negligible absorption, the rate of change of transmission with respect to optical path is maximum when the cavity phase $\beta$, equal to $2\pi \, ndcos(\theta)/\lambda$ takes on values near $0.1$ or $0.9\pi$ and all others differing from these by a multiple of $\pi$. Biasing the Fabry-Perot interferometer at such values of $\beta$ results in large transmission changes with small changes in optical path.

Figure 3A:
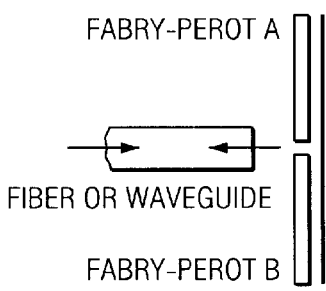
FIG. 3 is a diagram showing example configurations of a fiber-coupled MEMS realization of the basic interferometric micro-sensor: (a) Reflective configuration; (b) Transmissive configuration. In this example, the Fabry-Perot interferometers A and B are two separate adjacent MEMS structures.
Figure 3B:
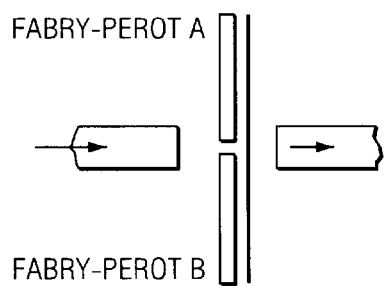
Figure 4A:
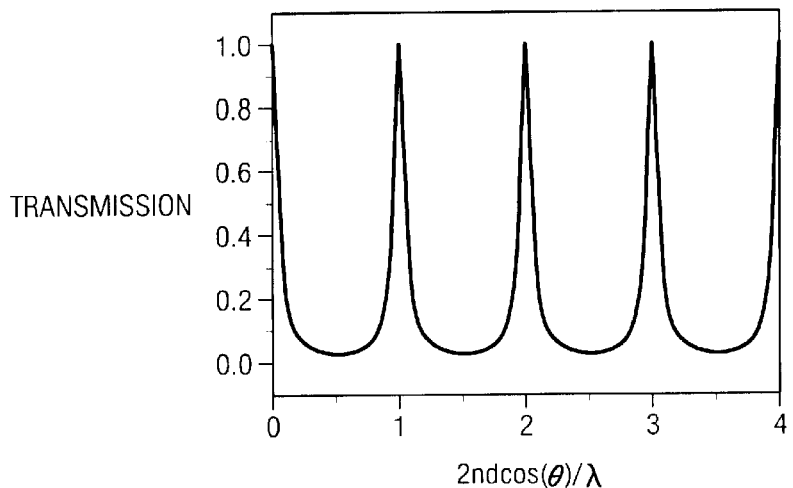
FIG. 4 is a diagram of transmission (a) and phase of transmitted field (b) of a Fabry-Perot interferometer with 30% reflectivity mirrors. Equivalent points on adjacent peaks of the transmission curve correspond to a PI phase shift, both of the cavity and of the transmitted field.
Figure 4B:
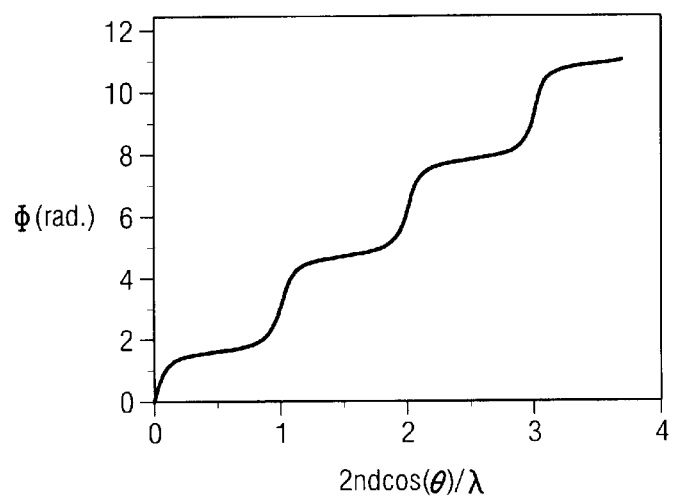
Figure 5:
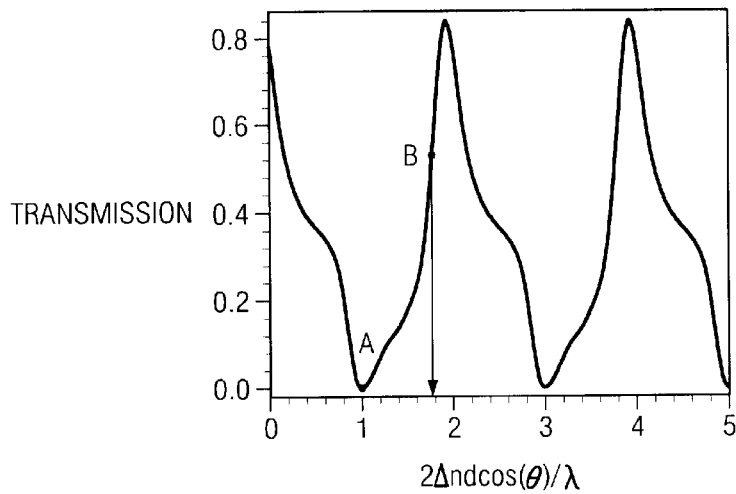
FIG. 5 is a diagram of an overlap integral of field transmitted through two Fabry-Perot interferometers and symmetrical waveguide mode showing transmission minimum (A) and transmission slope maximum (B)

The overall transmission of the basic structure depends not only on the transmission of the Fabry-Perot interferometers and the phase relation at the output port, but also on the efficiency of wave coupling at the output. In the realization of FIG. 3, the coupling of the reflected or transmitted waves from the two Fabry-Perot interferometers into single-mode fiber implements the second directional coupler of the Mach-Zehnder structure. FIG. 5 shows the overlap integral of transmitted field and fiber mode. The fiber mode is assumed to be symmetric about the fiber axis. The field transmitted through the Fabry-Perot interferometers biased near maximum transmission slope is taken identical to the input field except for interferometer phase, essentially a phase weighted fiber mode function.

The simplified geometry assumed here reduces the field-fiber mode coupling to mere interference between waves transmitted through the Fabry-Perot interferometers, suitably normalized. FIG. 5 shows that transmission minima occur where the phase difference between the waves is an odd multiple of $\pi$ and a steep transmission slope is found when the phase difference between the waves is near $1.8\pi$ or the sum of that and multiples of $\pi$.

For the application envisaged, apart from a bias determining. the operating point, the relative phase arises from static cavity phase changes in one Fabry-Perot cavity, namely, changes occurring in the refractive index of the medium within the cavity. In particular, one of the Fabry-Perot cavities may be treated to be selectively sensitive to some analytes, a component of a gas mixture, for example. Then adsorption of the gas on the substrate leading to refractive index changes in the interferometer cavity is registered at the output port as a phase change between the sample and reference arms. Consequently, the transmission of the device is altered, and a detector positioned to receive the transmitted field registers a change in intensity related to the quantity of adsorbed gas. Biasing at the position of maximum slope ensures large changes in detector signal for small changes in optical path.

Figure 6:
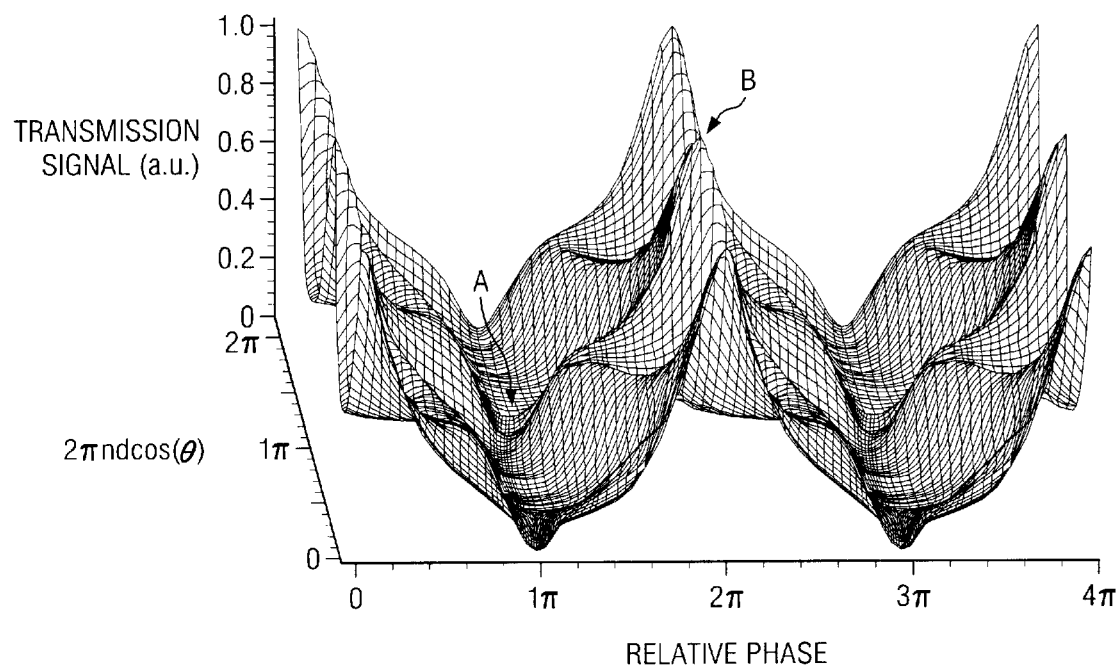
FIG. 6 is a more detailed view of operating space of interferometric micro-sensor showing transmission minimum (A) and transmission slope maximum (B)

The asymmetry of the transmission peaks appearing in FIG. 5 is shown more clearly in FIG. 6 where variation of transmission with cavity phase of the reference interferometer is also shown. Although extensive regions with near zero transmission exist within the global operating space, only restricted portions of the plot show. appreciable second derivative of transmission. An example of such a region is marked A on FIG. 6. Operating the sensor in those regions is expected to yield large changes in signal with near zero background when differential techniques are employed.

A number of improvement to the basic sensor can be implemented. Using multiple quarter-wave layer of high and low index materials can increase reflectivity of the Fabry-Perot mirrors. The sensitivity of the sensor is improved thereby. Phase sensitive detection provides a means for further improving noise immunity and resolving phase, excursions larger than $2\pi$. The method comprises in modulation the input field frequency and applying various filters to the resulting phase rotation at the output [8].

Figure 7:
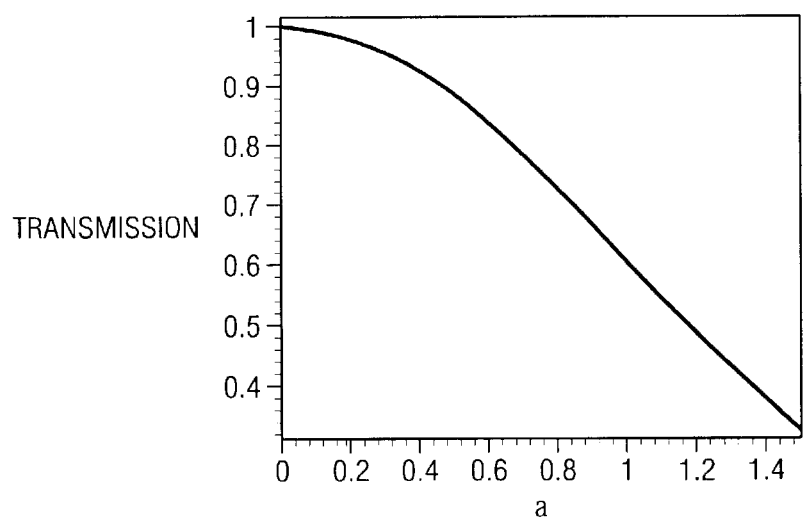
FIG. 7 is a diagram showing variation of transmission of interferometric micro-sensor with output fiber position. The horizontal axis represents the position, a, of the output fiber axis relative to the common axes of the input fiber and the Fabry-Perot pair, normalized to the fiber mode radius. Gaussian fiber and field spatial modes are assumed.
Figure 8A:
FIG. 8 is a diagram of one example of a fabrication process of a single-layer FIMS structure.
Figure 8B:
Figure 8C:
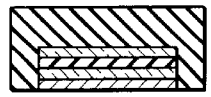
Figure 8D:
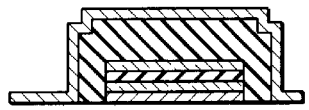
Figure 8E:
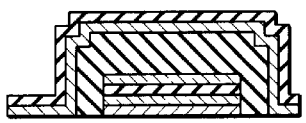
Figure 8F:
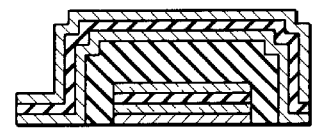
Figure 9A:
FIG. 9 is a diagram of one example of a fabrication process of a multi-layer FIMS structure.
Figure 9B:
Figure 9C:
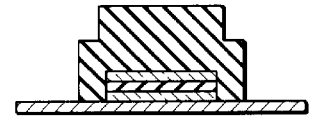
Figure 9D:
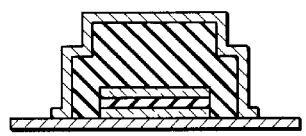
Figure 9E:
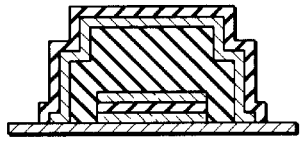
Figure 9F:
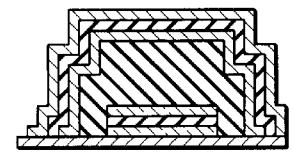
Figure 9G:
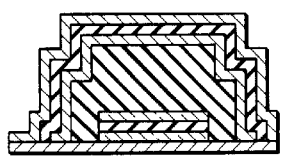
Figure 9H:
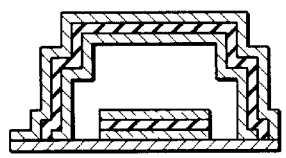

There are a number of challenges that need to be addressed in the FIMS device. Sample absorption may result in unequal intensities returned by the two Fabry-Perot interferometers. The resulting imbalance of the Mach-Zehnder interferometer will then lead to a large background that may not be removable by the differential detection. The top layers of the two FPI's need to separated so that they do not become attached, yet a large gap is not permissible since light will simply pass through the gap and ruin the contrast ratio. One means of circumventing this difficulty is to separate the two top layers into equivalent planes that are separated from each other in the vertical direction by an integer number of half wavelengths. Additionally, there is a trade-off between the bandwidth and contrast ratio of atypical Fabry-Perot interferometer. Also, the optimization of the bias point for the sensor may be a multi-dimension space with non-unique solutions. Since the splitter in the realization of FIG. 3 cannot be adjusted without disrupting symmetry, another means is necessary to balance the signal levels in the arms to assure high contrast. Symmetry plays a significant role in achieving a high throughput. Maintaining an acceptable performance may require actively aligning the axes against vibration and other perturbations that may lead to significant deviation from collinear geometry. Acceptable tolerance on alignment is suggested by FIG. 7 which shows variation of the transmission with output fiber axis position, relative to the axes of the input fiber and coupler.

FABRICATION TECHNIQUES FOR FIMS

The fabrication process of the FIMS structure comprises mature semiconductor thin film technique such as the low-pressure chemical vapor deposition (LPCVD), reactive ion etching (RIE), wet etching techniques, and photo-lithography. FIG. 8 describes the process flow of the FIMS fabrication.

The fabrication starts with a silicon substrate doped with phosphorous (n-type doping). On the substrate, two layers of thin films are deposited. The first one is a 193 nm (quarter-wavelength for 1550 nm in SiN) layer of SiN deposited by LPCVD method. This layer functions as an electrical isolation layer as well as a part of the multiple-layer mirror. On the top of the layer, a 103.3 nm (quarter-wavelength in poly-si) thick layer of poly-silicon (PS I) is deposited by LPCVD on the top of the SiN layer. The two layers constitute the lower mirror of the Fabry-Perot (FP) structure. The resultant cross-section is give in FIG. 8.1.

The lateral shape and size of the segmented FP structure are defined using standard photo-lithographic techniques. A thin layer of photoresist is deposited on the PS I layer using spinner. The wafer is then soft-baked in 75 to 100° C. for 10 minutes to remove the built-in stress and residual solvent. The desired pattern is transferred by exposing the coated surface to UV light through the patterned mask. Then a relief image that will function as the etch-mask is formed by dissolving the exposed portion of the coating with chemical processes. The hardness of the patterned photoresist can be improved by hard-baking the surface in 120° C. for 20 minutes. The uncovered portion of PS I layer is then dry-etched by RIE method. $SF_6$/He mixture is a popular etchant for poly-silicon. Finally the photoresist is removed with liquid resist-strippers or dry resist ashing technique. FIG. 8.2 shows the patterned and etched poly-silicon layer.

A phosphosillicate glass (PSG) sacrificial layer is deposited with thickness of 775 nm (half-wavelength in air). This can be achieved by doping the SiO2 with phosphorus during LPCVD process. To reduce the mechanical stress of the structure a one-hour thermal annealing in 1050° C. Argon gas is performed. Following the deposition process, the shape of the sacrificial layer is tailored by another set of pattern transfer and etching process. RIE with $CF_4+CHF_3+$ He (90:30:120 sccm) can be utilized for dry-etching of PSG. The result is given in FIG. 8.3. Another quarter-wavelength layer of poly-silicon is deposited (PS II) by LPCVD. Then a new set of patterning and etching is performed to shape the PS II layer. With the completion of PS II patterning an etching, the FP structure with two segmented movable upper layers is formed (FIG. 8.4).

The last patterning process follows to install three metal (A1) contacts. Two of them are connected to the two upper poly-silicon segments that will function as upper electrodes. The other will be used for the common lower electrode. The lift-off process is utilized for this process. By covering the structure with photoresist first and then depositing the contact material, the process of metal etching can be avoided. The cross-sectioned structure is shown in FIG. 8.5.

The sacrificial layer is removed and the structure is released by immersing the whole structure in 49% HF solution. The following rinsing process with DI water and alcohol helps reduce the stiction. Baking the released structure at 1100° C. for 10 minutes completes the fabrication process. FIG. 8.6 shows the cross-section of the completed single-layer FIMS structure.

As described in FIG. 9, the fabrication of multi-layer FIMS structure requires additional deposition steps for implementing the multi-layer dielectric mirrors. Starting from FIG. 9.1 to FIG. 9.2, two quarter-wavelength layers of SiN and poly-silicon are deposited and patterned in alternate fashion to form the lower multi-layer mirror. Then the deposition and patterning of sacrificial layer follows as shown in FIG. 9.3. The upper mirror structure comprises two poly-silicon layers and a SiN layer. Again each layer has the thickness of quarter-wavelength. To define the lateral and cross-sectional structure of the segmented FP structure, patterning and RIE is performed after the deposition of each layer (from FIG. 9.4 to FIG. 9.6). On the top of that, another set of patterning and lift-off process is performed to install metal contacts for the electrodes. The poly-silicon layers at the lowest of the upper mirror and at the top of the lower mirror are used as electrodes (FIG. 9.7). Finally the structure is released by wet etching with HF (FIG. 9.8). In the fabrication of multi-layer structure, the build-up of mechanical stress due to deposition of different materials is the main issue in this case. Thermal annealing process needs to be performed to reduce the stress.

Although the present invention has been described in several embodiments, a myriad of changes, variations, alterations, transformations, and modifications may be suggested to one skilled in the art, and it is intended that the present invention encompass such changes, variations, alterations, transformations, and modifications as fall within the spirit and scope of the appended claims.

REFERENCES

1. J. Dakin and B. Culshaw (eds.), Optical Fiber Sensors Vol. 3: Components and subsystems, (Artech House, Norwood, Mass. 1988).
2. G. T. A. Kovacs, *Micromachined Transducers Sourcebook*, (McGraw-Hill, Inc., New York, N.Y. 1998).
3. J. H. Jerman and S. R. Mallinson, in Technical Digest of the IEEE Solid State Sensors and Actuators Workshop, Hilton Head, 1988, (reprinted by EG&G IC Sensors, Milpitas, Calif.).
4. A. Brandenburg, R. Edelhauser, and F. Hutter, Sensors & Actuators B 11, 361 (1993).
5. H. George, U. Hollenbach, J. Sochtig, and W. Sohler, in *Integrated Optics*, edited by H. Nolting and R. Ulrich, (Springer, Berlin, 1985); C. Erbeia, S. Valette, J. Jadot, P. Gidon, and S. Renard, in *Optical Fiber Sensors*, edited by H. Arditty, J. Dakin, and R. Kersten, (Springer, Berlin, 1989); M. Ohkawa, M. Izutsu, and T. Sueda, Jpn., Appl. Phys. 28, 287 (1989).
6. K. Aratani, P. J. French, P. M. Sarro, D. Poenar, R. F. Wolffenbuttel, and S. Middelhoek, Sensors & Actuators A 43 17 (1994).
7. C. Marxer, M. A. Gretillat, V. P. Jaecklin, R. Baettig, O. Anthamatten, P. Vogel, and N. F. de Rooij, Sensors & Actuators A 52, 46 (1996).
8. A. Dandridge and A. B. Tveten, Opt. Lett. 7, 279 (1982); D. A. Jackson, A. D. Kersey, M. Corke, and J. D. C. Jones, Electron. Lett. 18, 967 (1982); 18, 967 (1982).

What is claimed is:

1. An optical processing device comprising:
   an Mach-Zehnder interferometer comprising:
      a reference arm comprising a first Fabry Perot interferometer; and
      a sample arm comprising a second Fabry Perot interferometer including at least two mirrors forming a Fabry-Perot cavity therebetween, and an absorbing material disposed within the cavity;
   wherein the Fabry-Perot interferometer in the sample arm permits a first portion of an input signal to pass multiple times through a sample while a second portion of the input signal passes through the reference arm, and wherein the first and second signal portions are combined at an output to result in constructive or destructive interference between the signal portions.

2. The optical processing device of claim 1, wherein at least one of the interferometers operates as a chemical or a biochemical sensor.

3. The optical processing device of claim 1, wherein at least one of the interferometers operates as an optical switch.

4. The optical processing device of claim 1, wherein at least one of the interferometers operates as an optical attenuator.

5. The optical processing device of claim 1, wherein the reference and sample arms interface with a single mode fiber.

* * * * *